United States Patent [19]
Say

[11] Patent Number: 5,662,627
[45] Date of Patent: Sep. 2, 1997

[54] ASPIRATION APPARATUS

[75] Inventor: Samuel L. Say, La Canada, Calif.

[73] Assignee: SSCOR, Inc., Sun Valley, Calif.

[21] Appl. No.: 512,803

[22] Filed: Aug. 9, 1995

[51] Int. Cl.[6] .................... A61M 1/00; A61M 15/00; A47L 5/24
[52] U.S. Cl. ................ 604/319; 804/35; 804/322; 128/200.24; 15/344
[58] Field of Search .................. 604/319–323, 604/35, 131; 128/200.24, 205.12; 15/339, 344

[56] References Cited

U.S. PATENT DOCUMENTS

| | | | |
|---|---|---|---|
| 3,915,189 | 10/1975 | Holbrook et al. | 604/319 |
| 4,033,511 | 7/1977 | Chamberlin | 239/346 |
| 4,899,418 | 2/1990 | Steiner et al. | 15/344 |
| 4,934,020 | 6/1990 | Jackson | 15/339 |
| 5,065,745 | 11/1991 | Meier | 128/205.12 |
| 5,134,994 | 8/1992 | Say | 128/200.24 |
| 5,466,229 | 11/1995 | Elson et al. | 604/319 |

Primary Examiner—John G. Weiss
Assistant Examiner—David J. Cho
Attorney, Agent, or Firm—Christie, Parker & Hale, LLP

[57] ABSTRACT

A portable aspirator having a rigid lightweight housing fabricated by rotational molding. The housing has a smooth outer surface to allow for the easy cleaning and disinfecting of human fluids, thereby preventing the spread of disease by blood-borne pathogens. A shelf, which can be attached an inner wall of an ambulance patient compartment, can secure the portable aspirator in position up to loadings of 25 g's. When secured into position, a battery recharging circuit is completed allowing for the recharge of the portable aspirator batteries.

31 Claims, 8 Drawing Sheets

ASPIRATION APPARATUS

FIELD OF THE INVENTION

The present invention relates to a battery operated portable rechargeable aspirator.

BACKGROUND OF THE INVENTION

In recent years, portable aspirators have gained popularity, in part due to an increased awareness of the need for sanitary aspiration techniques for avoiding the spread of disease. These aspirators are often used by fire fighters, paramedics, and other rescue and health workers. Most portable aspirators in use today have a soft material housing, typically made of fabric. Human fluids often get trapped into the woven structure of the fabric creating areas fostering blood-borne pathogens. These pathogens can spread disease to both the rescue/health worker using the aspirator or a successive patient. The health and rescue industries are in need of a portable aspirator having a lightweight housing fabricated from a smooth, rigid material such that the outer surface of the housing does not have any crevasses to trap any human fluids fostering the growth of blood-borne pathogens.

Ambulances, especially those used in foreign countries, have very small patient compartments. In addition, in most countries, any device stored in an ambulance must be capable of withstanding a 25 g loading without becoming unsecured. Due to the restricted space and the 25 g loading requirement, in many situations portable aspirators are precluded from being carried in the patient compartment. A shelf, therefore, that can be mounted to a inner wall of the patient compartment, such that it does not take up any of the useful compartment floor space and which is capable of keeping the portable aspirator secured at loadings of up to 25 g's, is much needed by the health and rescue industries around the world.

Typically, after a portable aspirator has been used, the aspirator is plugged into a power unit to recharge its batteries. If a portable aspirator finds many continuous uses in one day while out in rescues with an ambulance, its battery may run dead preventing its further use. A system, therefore, that allows the portable aspirator to be recharged while being securely transported within the ambulance can provide a great benefit to the health and rescue industries.

SUMMARY OF THE INVENTION

The present invention is a portable aspirator which is fabricated from a lightweight rigid material, such as linear polyethylene, by rotational molding. The housing has a smooth outer surface which allows for easy cleaning and disinfecting preventing the accumulation of blood-borne pathogens. A shelf is specifically designed such that it can be connected to a wall of an ambulance. The shelf has means for easily securing the portable aspirator in place when the aspirator is placed on the shelf. When the aspirator is secured by the shelf, two recharge sockets on the aspirator make contact with two matched charging plugs on the shelf. The plugs are connected to a power source, such as the vehicle battery in an ambulance. Once this contact is made, sufficient recharge power is provided to the recharge socket until the batteries of the portable aspirator are completely recharged. The shelf has a handle which allows for the quick release of the portable aspirator.

DETAILED DESCRIPTION

The invention is an aspirator having a lightweight rigid material housing 2 (FIG. 8) formed by rotational molding. The rotational molding process is well known in the art. The housing is typically made from linear polyethylene. It is lightweight and it has a smooth outer surface and a rougher inner surface. The smooth outer surface allows for easy cleaning and disinfecting of the housing exterior preventing the accumulation of blood-borne pathogens. The housing has four openings providing access to the housing interior: (a) a bottom opening 4 which allows for the installation of the aspirator working components (i.e., the equipment for generating suction including a rechargeable battery to power the equipment); a front opening 6 to accommodate a panel with the aspirator operating controls; and two side openings 8 to accommodate two recharge sockets for connecting a power source to recharge the rechargeable battery. These openings are protected by gaskets to repel water, and protect the components housed in the housing during a "hose down" precleaning process.

The working components of the invention are described in U.S. Pat. No. 5,134,944, with the exception that the present invention has two sets of recharge sockets instead of one. U.S. Pat. No. 5,134,944 is incorporated herein by reference.

Figure 1:
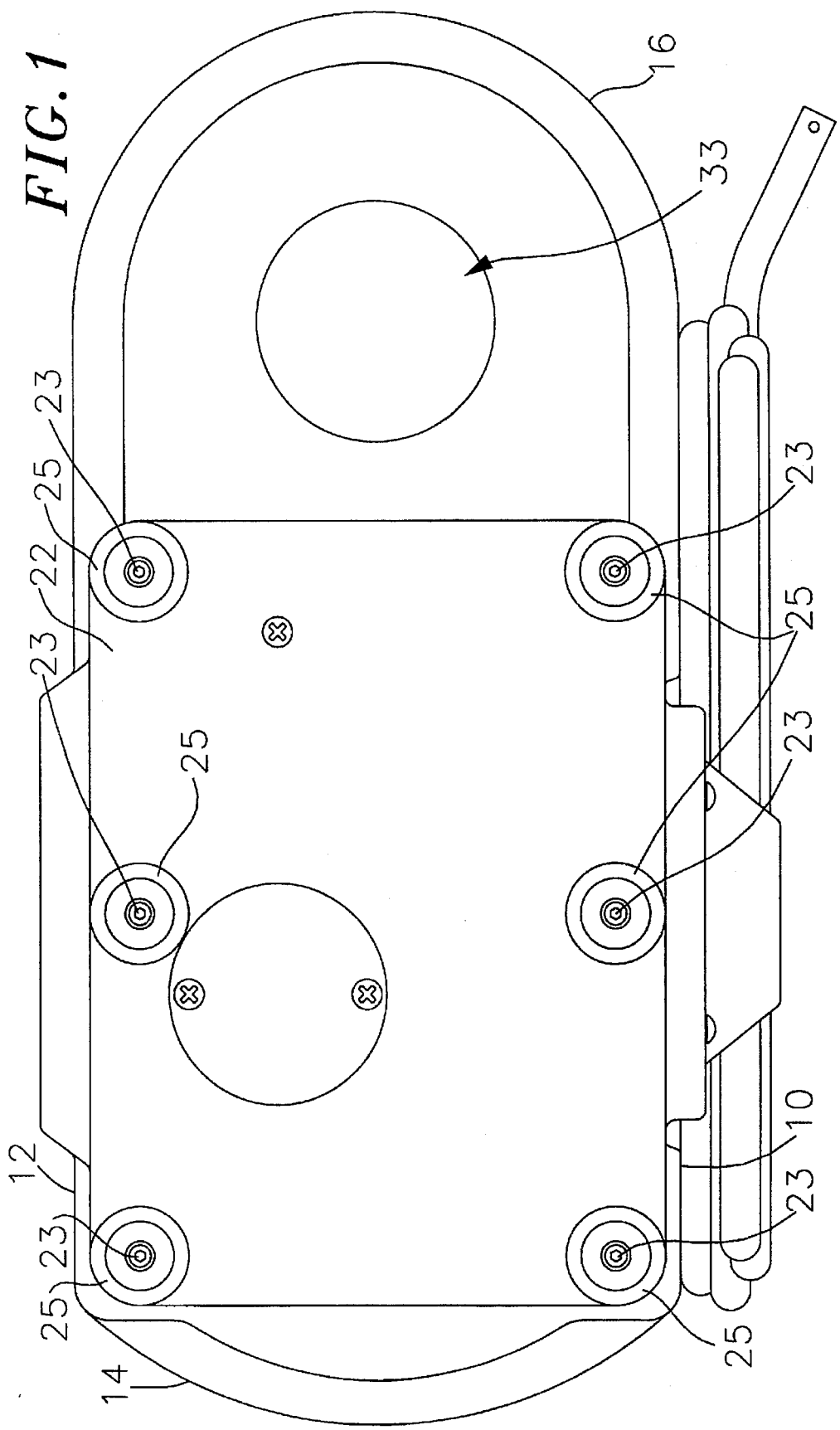
FIG. 1 is a bottom view of the portable aspirator.
Figure 8:
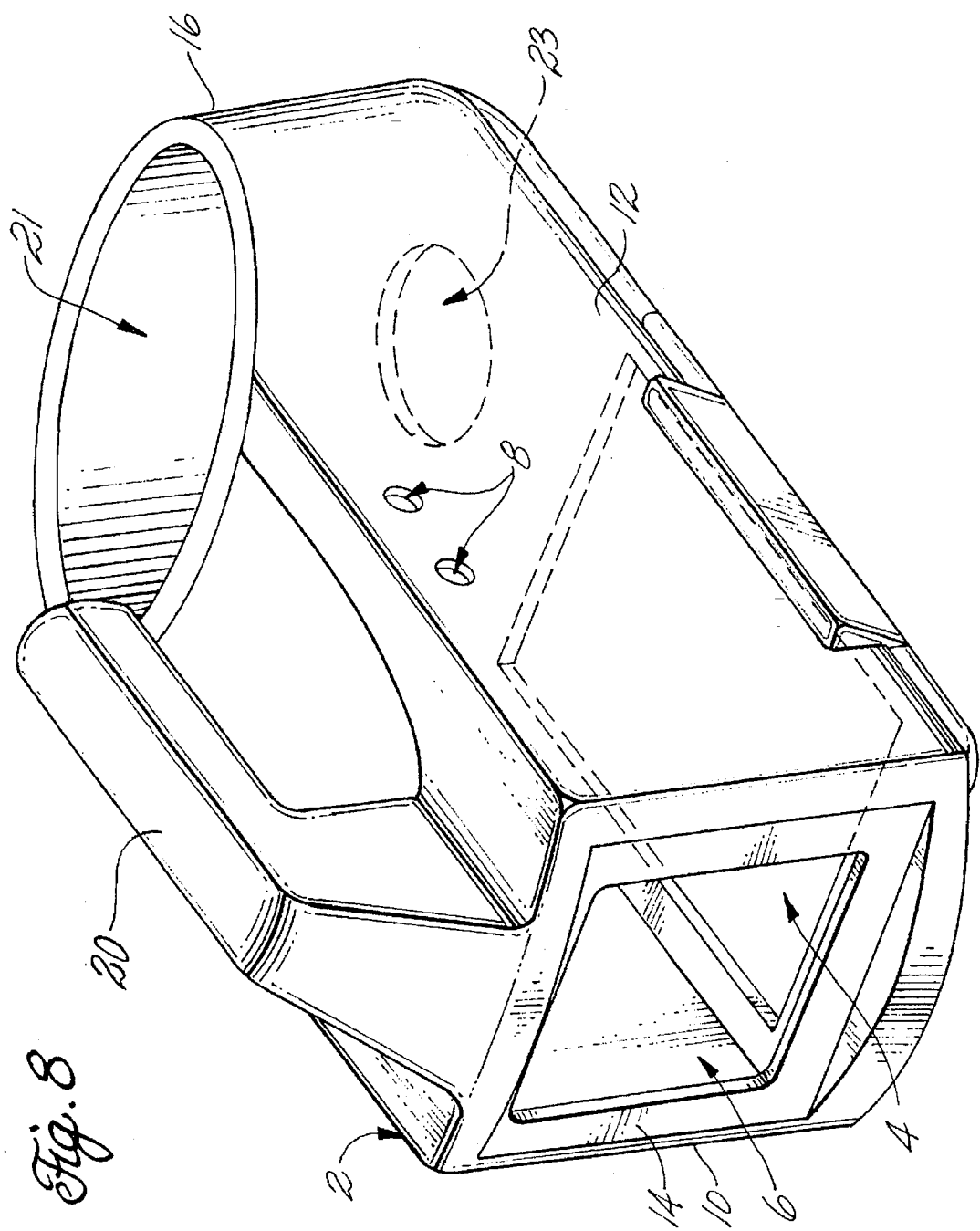
FIG. 8 is an isometric view of the portable aspirator molded housing.

The housing has an oblong shape (FIGS. 1 and 8). It has a first 10 and a second 12 parallel longer sides and parallel shorter sides 14, 16. One of the shorter sides 16 is curved to accommodate a container 18 for collecting the suctioned fluids. The container is quickly and easily replaceable so that multiple patients can be handled in rapid succession. The housing includes a handle 20 for portably transporting the aspirator. Proximate the curved side, the housing has a cylindrical depression 21 to accommodate the container 18. An opening 33 at the bottom of the depression allows for drainage of any fluids that may have overflowed from the container.

The bottom opening 4 is covered by a metal plate 22. The metal plate has a sealing gasket (not shown) so that when the metal plate covers the opening, the sealing gasket makes contact with the area of the housing proximate the perimeter of the opening. As a result, when the metal plate is attached, the sealing gasket seals the metal plate-housing interface forming a water proof seal. The bottom plate is attached to the housing using six fasteners 23. A rubber leg 25 is located at each corner and center side of the bottom plate and is connected to the bottom plate and housing using fasteners 23 which also connect the bottom plate to the housing. The housing has a vent 27, shown in FIGS. 2 and 3, for venting the components sealed inside the housing. The vent is located on the shorter side 14 away from the container and is positioned on an inclined portion 29 of the side such that the vent faces downwards. This minimizes the risk that any contaminants will enter the housing through the vent.

To facilitate installation, the working components of the aspirator are connected to the metal plate 22. The metal plate with the connected components is then inserted from the bottom opening 4 into the housing.

The shorter side 14 of the housing (FIGS. 2 and 8) has the opening 6 which accommodates a switch panel 24 to which are attached an on/off switch 26, a suction regulator controller 28, and a battery recharge socket 30. After the plate containing the working components is attached to the bottom opening of the housing, the three control switches are connected to the appropriate components. A gasket 32 is incorporated between the plate containing the switches and the side of the housing. The switch panel and gasket are then fastened to the side of the housing using four fasteners 34. When fastened, the gasket forms a tight water proof seal.

The recharge socket 30 is matched to a power source plug which supplies power for recharging the battery. A cap 31 connected about the periphery of the socket is used to cover the socket when the aspirator is being used in order to prevent any human fluids from contaminating the socket.

Figure 3:
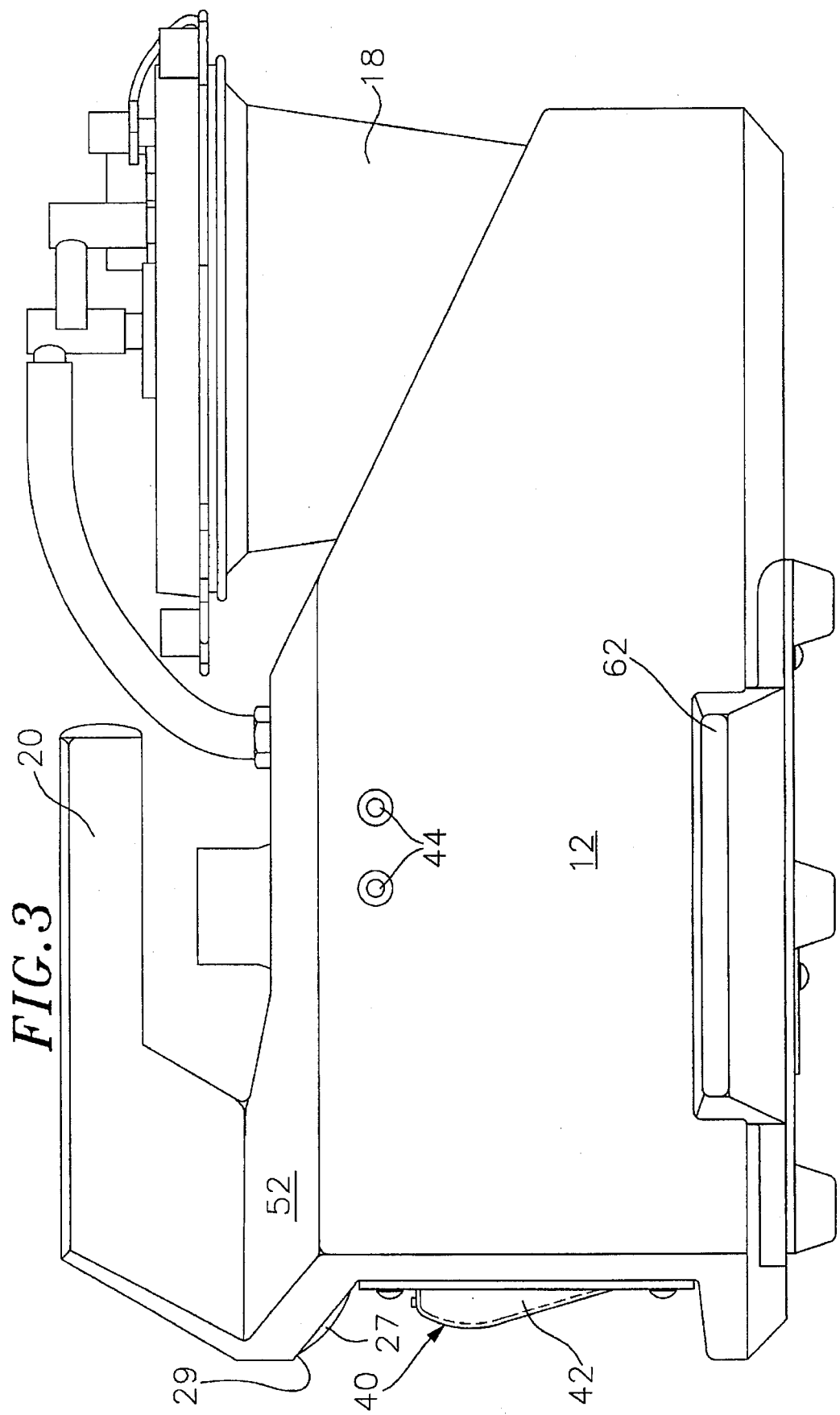
FIG. 3 is a side view of the portable aspirator.

The on/off switch 26 is water proof and sits inside a channel shaped member 40. The channel member legs 42 are contoured to the shape of the switch while in the off position, as shown in FIG. 3. This design prevents one from accidentally turning the aspirator on. In order to turn the aspirator on, one must make contact with a switch only. When one accidentally hits the panel, she/he would more than likely make contact with the contoured legs which would prevent the accidental depression of the on/off switch.

Two recharge sockets 44 are connected to the second longer side 12 of the housing, as shown in FIG. 3, proximate the housing top. The sockets are mounted to the housing through openings 8 (FIG. 8). A gasket (not shown) is incorporated to tightly seal and waterproof the socket-housing interface.

Figure 4:
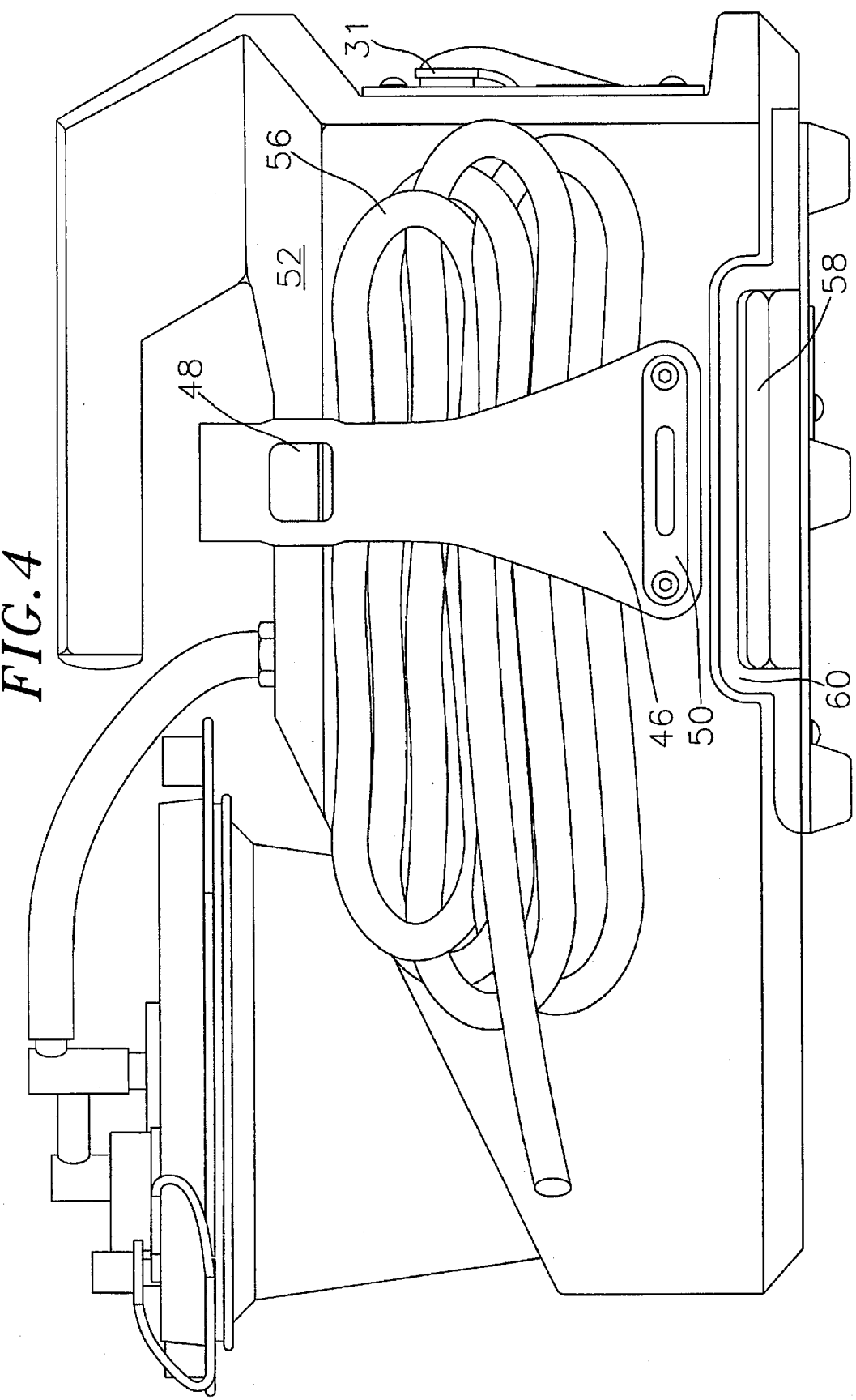
FIG. 4 is a side view of the portable aspirator, depicting the side opposite of FIG. 3.

A rubber strap 46 is attached to the first longer side 10 of the housing, as shown in FIG. 4. The strap is tapered from a wider end to a narrower end. The strap has an opening 48 proximate its narrow end. The wider end is connected approximately one inch from the housing bottom using a metal bracket 50 fastened to the housing side. The top side of the housing is relatively flat. Each of the longer sides of the housing joins the flat top side of the housing via an inclined portion 52. A latch 54 in the shape of a hooked plate is fastened to the inclined portion of the housing proximate the first longer side 10. A hose 56 which is used for suctioning is coiled and placed against the first longer side of the aspirator between the metallic bracket used to fasten the strap wide end and the latch. The rubber strap is then stretched over the coiled hose and is hooked to the latch through its opening. The length of the strap is chosen such that the strap is stretched when hooked to the latch. Stretching of the rubber strap provides the necessary force to maintain and store the hose against the side of the housing.

Figure 2:
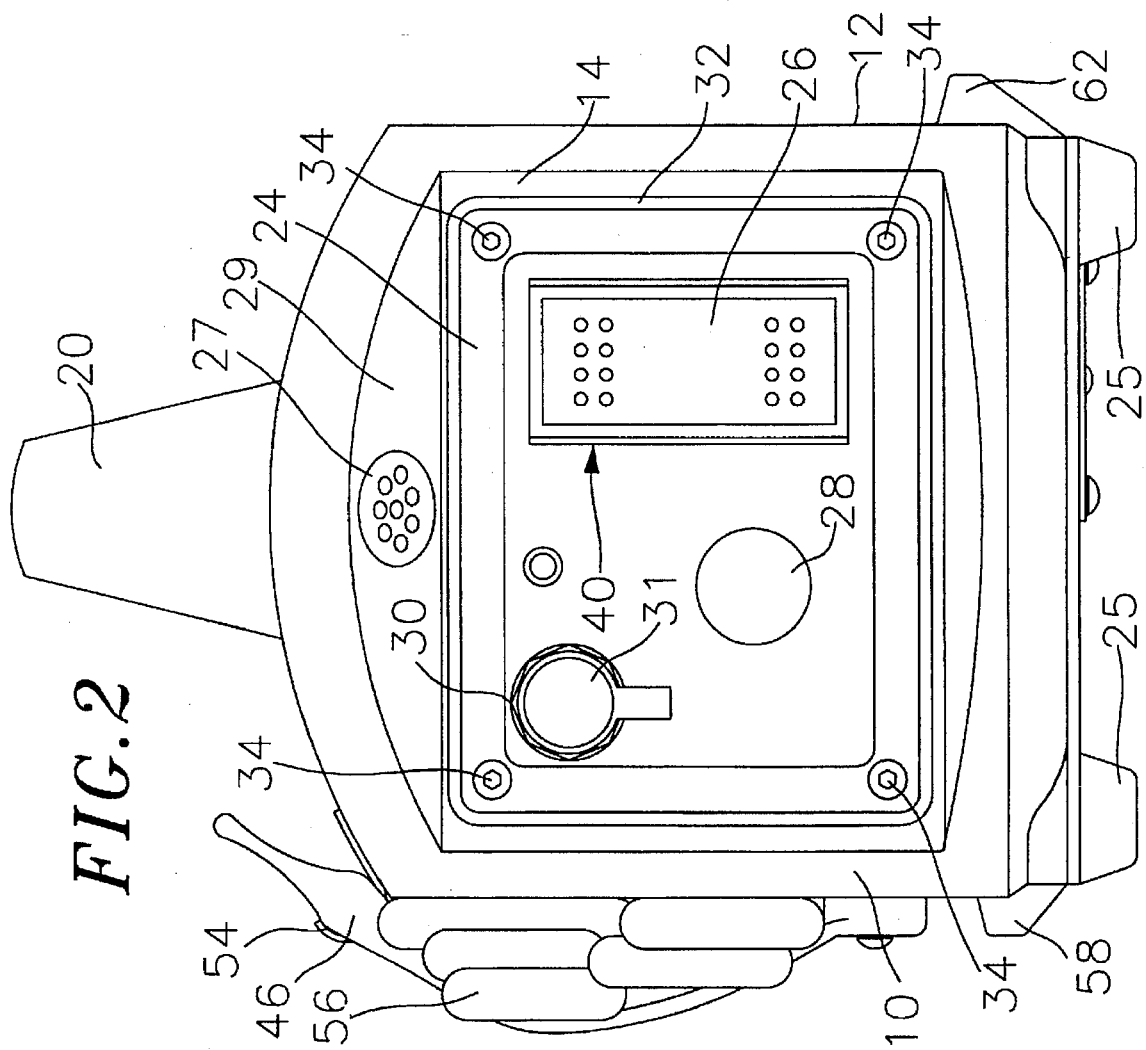
FIG. 2 is a front view of the portable aspirator.

Just below the location where the metallic bracket fastens the rubber strap, the housing has a first horizontal lip section 58. A groove 60 is formed where the lip section intersects the side of the housing. A similar second lip section 62 extends outwardly from the second longer side of the housing, as shown in FIGS. 2 and 3. These horizontal lip sections provide a means for holding down the aspirator in place, securing it for storage as described in detail below.

Figure 5:
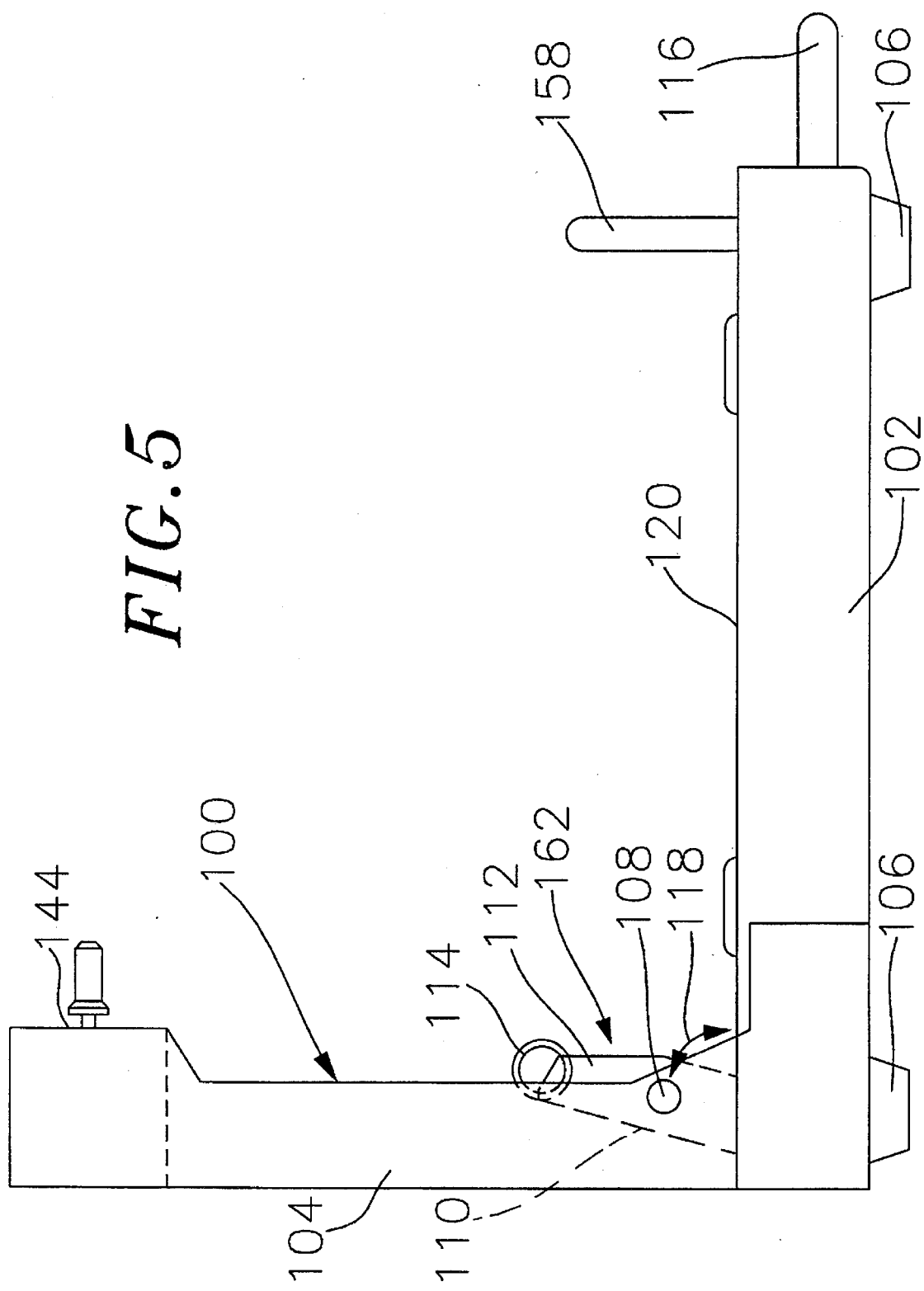
FIG. 5 is a side view of the securing shelf.

A securing shelf 100, shown in FIG. 5, is used to mount and clamp the aspirator in place and simultaneously recharge its battery. This shelf can be attached at any location on the interior surface of an ambulance and provides a convenient way of storing the aspirator in place. The shelf is designed to hold the aspirator in place at aspirator loads of 25 g's. Twenty-five g's is a load requirement that must be sustained by all objects stored in an ambulance.

The shelf has a planform horizontal member 102 and a vertical member 104. The members are fastened together forming an "L" shape. Legs 106 are attached to the bottom of the horizontal member, while the vertical member has openings (not shown) to accommodate fasteners for fastening the shelf to a surface, such as the wall of an ambulance.

Proximate the intersection between the horizontal and vertical members, a locking plate 162 is pivotally mounted to the vertical member using a pivot pin 108. A portion (not shown) of the locking plate extends into the horizontal member. The locking plate has a web 110 as well as two flanges 112 extending perpendicular to the web section. The flanges are parallel to each other. The flanges and web form a channel shaped member. The locking plate is pivoted about the pivot pin 108 approximately midway along the length of the flanges. The pivot pin penetrates both flanges. On the upper edge of the web is attached a cylindrical member 114 tangential to the web. The edges of the cylindrical member are attached to the flange edges. The bottom portion of the locking plate, which is located inside the horizontal member, is linked to a channel shaped handle 116 which protrudes beyond the edge of the horizontal member opposite the end connected to the vertical member. When the handle is pulled, it pulls on the bottom of the locking plate rotating it around the pivot pin. The locking plate is spring loaded (not shown) such that it forms an acute angle 118 with the horizontal plate. When the lever is pulled, a force is exerted against the spring loading to rotate the locking plate to an almost vertical position. When the handle is released, the spring loading forces the lever back into its original position and the locking plate rotates forming its original acute angle with the horizontal member (FIG. 4).

At the top surface 120 of the horizontal member and proximate the end opposite the vertical member is connected a channel shaped rod member 158 such that it forms a upside down "U". This member is designed so as to fit in the groove 60 formed between the first lip section 58 and the first longer side 10 of the housing.

On the upper portion of the vertical member are attached two plugs 144 which are matched to the two recharge sockets 44 located on the second longer side 12 of the housing. The plugs are connected to a power source which provides the appropriate power for recharging the battery. In an ambulance, the power source can be the vehicle battery or other power source or even other batteries which are recharged by the vehicle electrical system.

Figure 6:
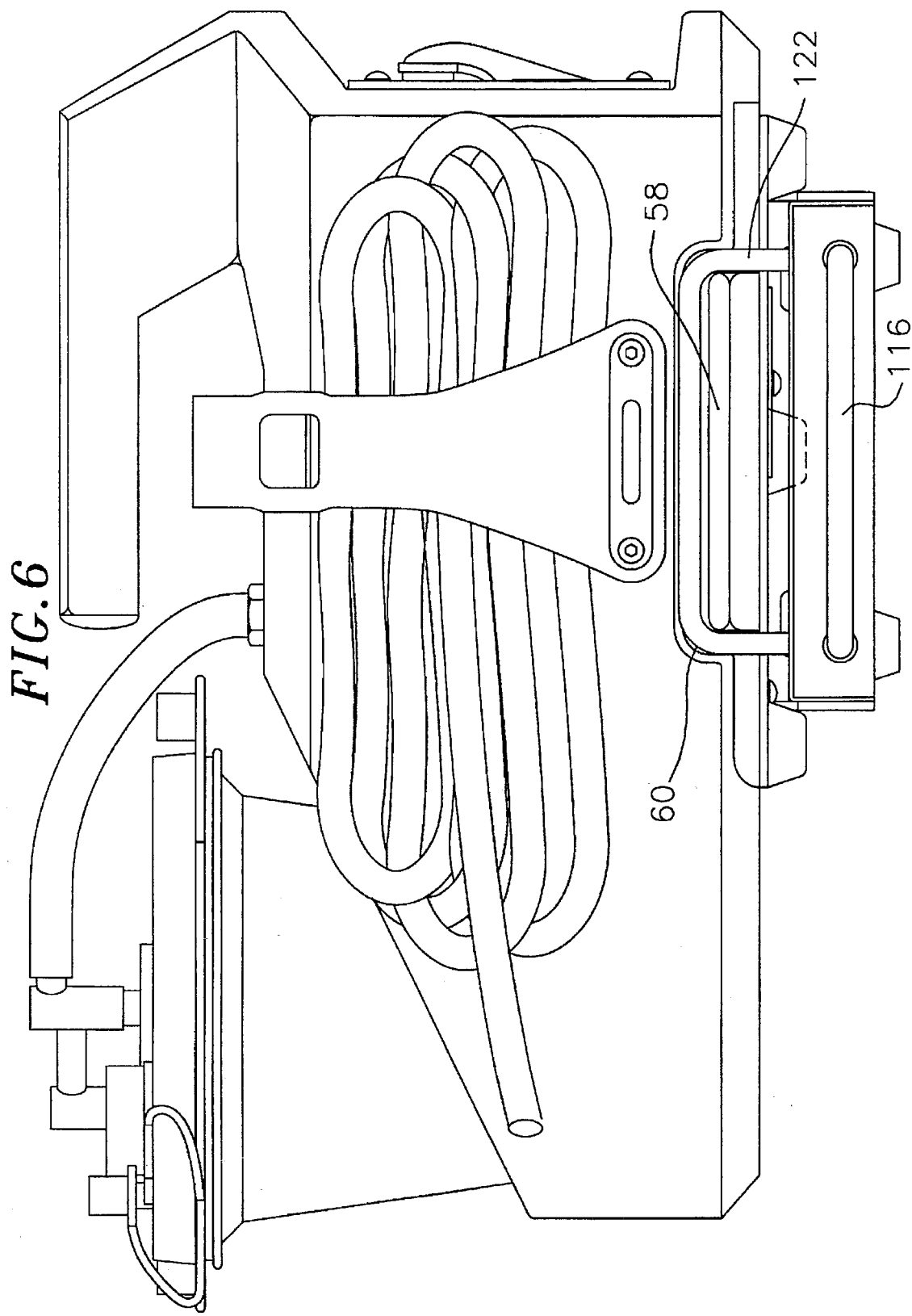
FIG. 6 is a side view of the portable aspirator mounted in the securing shelf.
Figure 7:
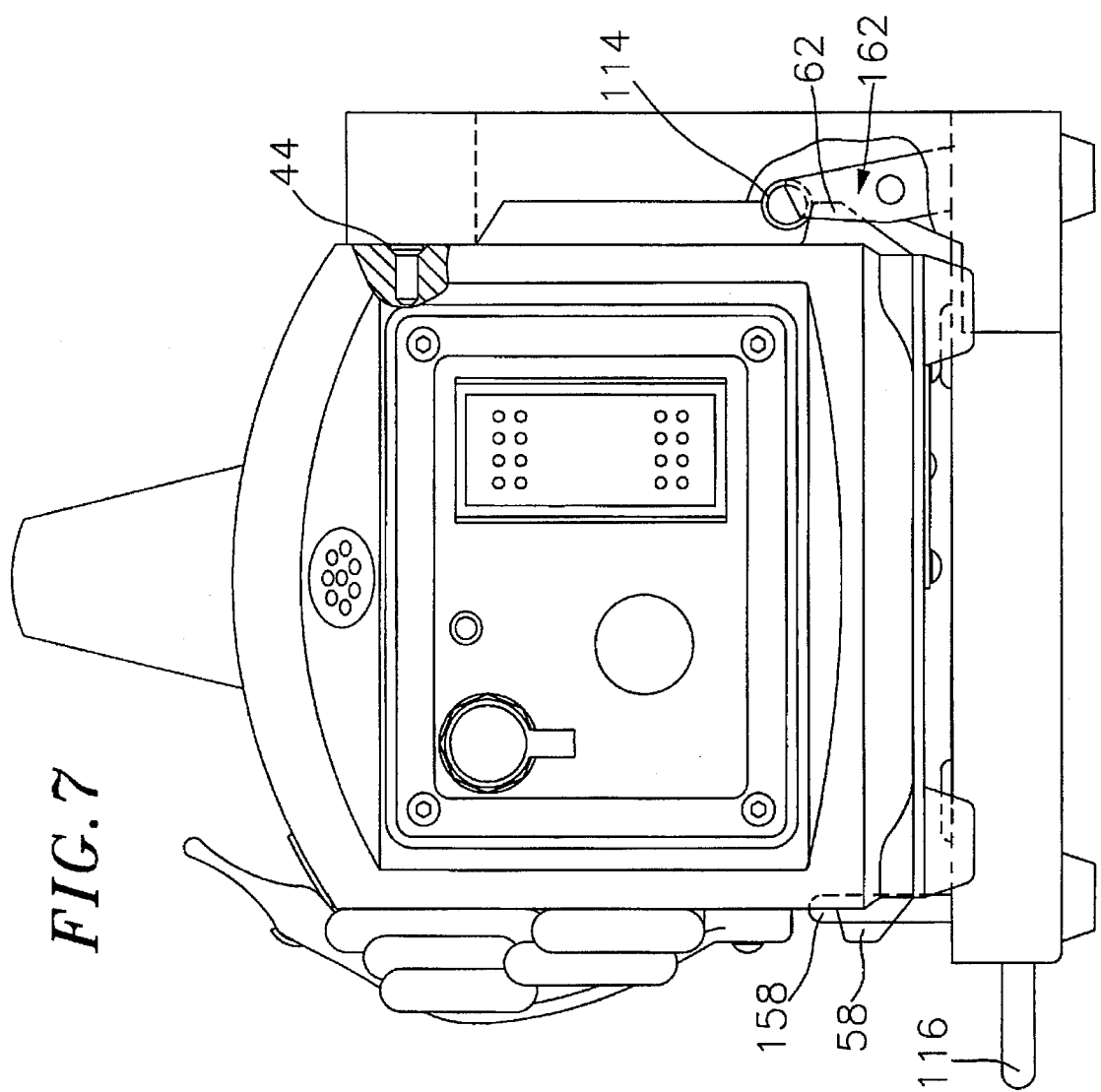
FIG. 7 is a front view of the portable aspirator mounted in the securing shelf.

To secure the aspirator into the shelf, the aspirator is slightly rotated about its longitudinal axis such that the first lip section 58 is slid inside the shelf channel rod member 158 so that the rod member fits into the groove 60 as shown in FIG. 6. The aspirator is then pushed down against the shelf horizontal member 102 wherein the second lip section 62 makes contact with the cylindrical member 114 of the locking plate 162 causing the locking plate to rotate, against the spring loading, to an almost vertical position about the pivot pin 108, allowing the aspirator lip section 62 to slide past the locking plate so that the aspirator can sit flat on the shelf horizontal member. As the aspirator moves from the inclined position to an almost horizontal position against the horizontal member of the shelf, the second lip section 62 moves below the cylindrical member 114 of the locking plate allowing the locking plate, due to the spring loading, to rotate towards its original position such that the cylindrical member makes contact with the top surface of the lip section 62. The spring loading causes a force to be exerted by the cylindrical member of the locking plate against the top surface of the lip section holding the lip section in place. At the same time, the first lip section 58 is constrained by the channel rod member 158. As a result, the aspirator is secured on the shelf as shown in FIG. 7.

To remove the aspirator from the shelf, the channel shaped lever 116 is pulled rotating the locking lever against the spring loading such that the cylindrical member 114 of the locking plate rotates to an almost vertical position and out of the way of the second lip section 62. By exerting an upward force on the aspirator handle 20 and by inclining the aspirator slightly about its longitudinal axis, the second lip section is moved away from the locking plate, while at the same time the first lip section 58 is slid out from the channel rod member 158, freeing the aspirator so that it can be pulled off the shelf.

When the aspirator is secured onto the shelf, the power plugs 144 on the shelf vertical member mate with the recharge sockets 44 on the aspirator side and the battery in the aspirator automatically gets recharged.

Having now described the invention as required by the patent statutes, those skilled in the art will recognize modifications and substitution to the elements of the embodiments disclosed herein. Such modifications and substitutions are within the scope of the present invention as defined in the following claims.

What is claimed is:

1. A portable aspiration apparatus comprising:
   a rechargeable means for generating suction;
   a single-piece housing molded from a rigid material for encasing and providing a waterproof shield to the rechargeable means, wherein the housing comprises a first opening on the bottom of the housing to accommodate the means for generating suction, a second opening to accommodate controls for operating the apparatus, and a set of openings to accommodate a set of two recharge sockets;
   a container for collecting fluids using the generated suction; and
   an external depression on the housing for accommodating the container.

2. The aspiration apparatus as recited in claim 1 wherein the housing is made from linear polyethylene and formed using rotational molding.

3. The aspiration apparatus as recited in claim 2 wherein the housing a has a rough inner surface and a smooth outer surface.

4. The aspiration apparatus as recited in claim 1 having an opening at the bottom of the depression to allow for drainage of suctioned fluids spilled into external the depression.

5. The aspiration apparatus as recited in claim 1 further comprising a lip on each of two opposite sides, said lips located proximate the bottom of the housing providing handles for gripping the housing for mounting onto a shelf.

6. A portable aspiration apparatus system comprising:
   a portable aspiration apparatus comprising,
      a housing
         rechargeable means for generating suction, the rechargeable means disposed in the housing,
         a recharging connector located on the housing and connected to the rechargeable means, and
         holding means on the housing for providing a surface for securing the housing; and
   locking means for engaging and gripping the holding means, the locking means remaining engaged on the holding means at load levels of 25 g's.

7. The aspiration apparatus system as recited in claim 6 wherein the housing can be quickly mounted to and unmounted from the locking means.

8. The aspiration apparatus system as recited in claim 6 wherein the locking means comprises power means for supplying power to recharge the rechargeable means.

9. The aspiration apparatus system as recited in claim 8 wherein the locking means further comprises a power connector matched to the recharging connector, wherein the power connector is in-line to the power means, and wherein upon mounting of the housing into the locking means the power connector engages the recharging connector to allow for recharging of the rechargeable means.

10. A portable aspiration apparatus system comprising:
    a single-piece housing molded from a rigid material and having an external depression,
    rechargeable means for generating suction disposed in the housing wherein the housing provides a waterproof shield to the rechargeable means, and
    a container placed in the external depression for collecting fluids suctioned using the generated suction.

11. The aspiration apparatus system as recited in claim 10 wherein the housing has first and second longer sides opposite each other and first and second shorter sides opposite each other.

12. The aspiration apparatus system as recited in claim 11 further comprising a suction hose for suctioning fluids using the rechargeable means.

13. The aspiration apparatus system as recited in claim 12 further comprising means for securing the suction hose to a side of the device.

14. The aspiration apparatus system as recited in claim 13 wherein the hose is secured on the first longer side of the device and the means for securing the hose comprises:
    a latch connected to the device side proximate the top; and
    a flexible strap having top and bottom ends, wherein the bottom end is connected to the first longer side proximate the bottom of the device and in-line to the latch, wherein the strap has an opening proximate the top end, wherein the suction hose is placed against the side of the device and the strap is stretched over the hose and is hooked, through its opening, by the latch, securing the hose in place against the device side.

15. The aspiration apparatus system as recited in claim 11 wherein the housing is formed by rotational molding.

16. The aspiration apparatus system as recited in claim 15 wherein the housing is fabricated from linear polyethylene.

17. The aspiration apparatus system as recited in claim 10 wherein the housing has a smooth outer surface and a rough inner surface.

18. The aspiration apparatus system as recited in claim 15 wherein the means for generating suction fits in the housing through an opening in the housing bottom, wherein the opening is covered with a plate having a sealing gasket.

19. The aspiration apparatus system as recited in claim 18 wherein the housing has one opening on a side to accommodate a panel comprising:
    an on-off switch;
    control means for regulating suction; and
    a first recharge socket providing a hook-up point for recharging the rechargeable means.

20. The aspiration apparatus system as recited in claim 10 further comprising locking means for securing the device on a structure and keeping the device secure on the structure at load levels of 25 g's.

21. The aspiration apparatus system as recited in claim 20 further comprising holding means on the housing for providing a surface for securing the housing, wherein the locking means is connected to the structure and engages the holding means.

22. The aspiration apparatus system as recited in claim 21 further comprising a second recharge socket located on a side of the device providing a hook-up point for charging the rechargeable means.

23. The aspiration apparatus system as recited in claim 22 wherein the locking means comprises power means for supplying power for charging the rechargeable means.

24. The aspiration apparatus system as recited in claim 23 wherein the power means has a power plug matched to the second recharge socket, wherein the housing is secured by the locking means, the plug engages the socket allowing for charging the rechargeable means.

25. The aspiration apparatus system as recited in claim 21 wherein the locking means comprises means for quickly disengaging the locking means and unsecuring the device.

26. The aspiration apparatus system as recited in claim 21 wherein the holding means comprise a horizontal lip extending proximate a lower portion of each of the longer sides of the device.

27. The aspiration apparatus system as recited in claim 21 wherein the locking means comprises:

a horizontal member having a planform rectangular shape having an upper surface;

a vertical member connected at its lower portion with the end portion of the horizontal member;

a power plug matched to the second recharge socket of the housing, said plug located proximate the top of the vertical member;

a locking member for engaging the lip of the second longer side, said locking member pivotally mounted to the lower end of the vertical member and spring loaded to form an acute angle with the horizontal member, wherein the locking member comprises, a narrow rectangular web;

a flange perpendicularly extending from each narrow side of the web wherein said flange portions are tapered and have openings to accommodate the mounting pivot pin; and a cylindrical member connected tangentially to the upper-wide-side edge of the web and the upper edge of each flange, wherein the spring loading forces the cylindrical member against the lip on the second longer side securing the device in place;

a lever extending from the end of the horizontal member opposite the end connected to the vertical member, said lever connected to the bottom portion of the locking member below the pivotal mount, whereby pulling of the lever rotates the locking member about the pivotal mount against the spring loading to move the cylindrical member away from the lip of the second longer side releasing the lip; and a channel shaped member having vertical feet connected to the upper surface of the horizontal member proximate the end opposite the vertical member wherein the channel engages the first longer side horizontal lip.

28. A portable aspiration apparatus system for suctioning fluids comprising:

an aspirator apparatus comprising, an aspirator housing having a first side and a second side opposite to the first side, means for generating suction disposed in the housing, and a first lip extending from the first side of the housing; and a shelf for securing the aspirator, the shelf comprising a spring loaded locking member, wherein when the aspirator apparatus is placed on the shelf, the spring loaded locking member engages the first lip and remains spring loaded against the lip at 25 g load levels.

29. The aspirator apparatus system as recited in claim 28 wherein the aspirator housing further comprises a second lip extending from the second side of the housing and wherein the shelf further comprises a constraining member, wherein when the aspirator apparatus is placed on the shelf, the constraining member constrains a movement of the second lip.

30. The aspirator apparatus system as recited in claim 28 wherein the aspirator housing is a single-piece housing molded from a rigid material.

31. The aspirator apparatus system as recited in claim 28 further comprising:

an external depression on the housing; and a container for collecting the fluids suctioned, the container placed in the depression.

* * * * *